United States Patent
Schleyer et al.

(10) Patent No.: US 11,622,742 B2
(45) Date of Patent: Apr. 11, 2023

(54) MOTION SIGNAL DERIVED FROM IMAGING DATA

(71) Applicant: Siemens Medical Solutions USA, Inc., Malvern, PA (US)

(72) Inventors: Paul Schleyer, Knoxville, TN (US); Inki Hong, Knoxville, TN (US); Judson P. Jones, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 504 days.

(21) Appl. No.: 15/733,498

(22) PCT Filed: Mar. 27, 2019

(86) PCT No.: PCT/US2019/024211
§ 371 (c)(1),
(2) Date: Aug. 12, 2020

(87) PCT Pub. No.: WO2019/195044
PCT Pub. Date: Oct. 10, 2019

(65) Prior Publication Data
US 2021/0106301 A1 Apr. 15, 2021

Related U.S. Application Data

(60) Provisional application No. 62/652,942, filed on Apr. 5, 2018.

(51) Int. Cl.
*A61B 6/03* (2006.01)
*A61B 6/00* (2006.01)
*G06T 7/20* (2017.01)

(52) U.S. Cl.
CPC ............ *A61B 6/5264* (2013.01); *A61B 6/037* (2013.01); *A61B 6/4035* (2013.01); *A61B 6/466* (2013.01);
(Continued)

(58) Field of Classification Search
CPC ..... A61B 6/5264; A61B 6/037; A61B 6/4035; A61B 6/466; A61B 6/5205; A61B 6/5217; G06T 7/20
See application file for complete search history.

(56) References Cited

U.S. PATENT DOCUMENTS 6,490,476 B1 * 12/2002 Townsend ............. G01T 1/2985
250/363.04
6,915,004 B2 * 7/2005 Newport ............... G06T 11/005
382/168
(Continued)

FOREIGN PATENT DOCUMENTS

JP 2005177212 7/2005
WO 2017046674 3/2017

OTHER PUBLICATIONS

Paul J Schleyer et al: "Retrospective data-driven respiratory gating for PET /CT", Physics in Medicine and Biology; Institute of Physics Publishing, Bristol GB; vol. 54; No. 7, Apr. 7, 2009 (Apr. 7, 2009), pp. 1935-1950.
(Continued)

*Primary Examiner* — Shefali D Goradia

(57) ABSTRACT

Embodiments provide a computer-implemented method of deriving a periodic motion signal from imaging data for continuous bed motion acquisition, including: acquiring a time series of three dimensional image volumes; estimating a first motion signal through a measurement of distribution of each three dimensional image volume; dividing the time-series of three dimensional image volumes into a plurality of axial sections overlapping each other by a predetermined amount; performing a spectral analysis on each axial section to locate a plurality of three dimensional image volumes which are subject to a periodic motion; performing a phase optimization on each axial section to obtain a three dimensional mask; estimating a second
(Continued)

motion signal through the three dimensional mask and the time-series of three dimensional image volumes; and estimating a final motion signal based on the first motion signal and the second motion signal.

20 Claims, 7 Drawing Sheets

(52) U.S. Cl.
CPC .......... *A61B 6/5205* (2013.01); *A61B 6/5217* (2013.01); *G06T 7/20* (2013.01)

(56) References Cited

U.S. PATENT DOCUMENTS

| | | | | |
|---|---|---|---|---|
| 7,603,165 | B2* | 10/2009 | Townsend | G01T 1/1611 250/363.04 |
| 9,269,166 | B2* | 2/2016 | Hansis | G06T 7/0012 |
| 9,535,145 | B2* | 1/2017 | Demeester | A61B 6/037 |
| 9,778,382 | B2* | 10/2017 | Fenchel | A61B 5/7285 |
| 2005/0185758 | A1 | 8/2005 | Bruder et al. | |
| 2010/0185085 | A1* | 7/2010 | Hamilton | A61B 8/0858 382/128 |
| 2012/0078089 | A1* | 3/2012 | Wollenweber | A61B 6/5258 250/363.03 |
| 2016/0252597 | A1* | 9/2016 | Liu | G01R 33/5608 324/309 |
| 2019/0091963 | A1 | 3/2019 | Nyeboer | |

OTHER PUBLICATIONS

S. Vandenberghe et al: "Recent developments in time-of-flight PET", EJNMMI Physics, vol. 3, No. 1; Feb. 16, 2016 (Feb. 16, 2016), pp. 1-30.

International Search Report for Corresponding International Application No. PCT/US2019/024211, dated Jun. 13, 2019.

* cited by examiner

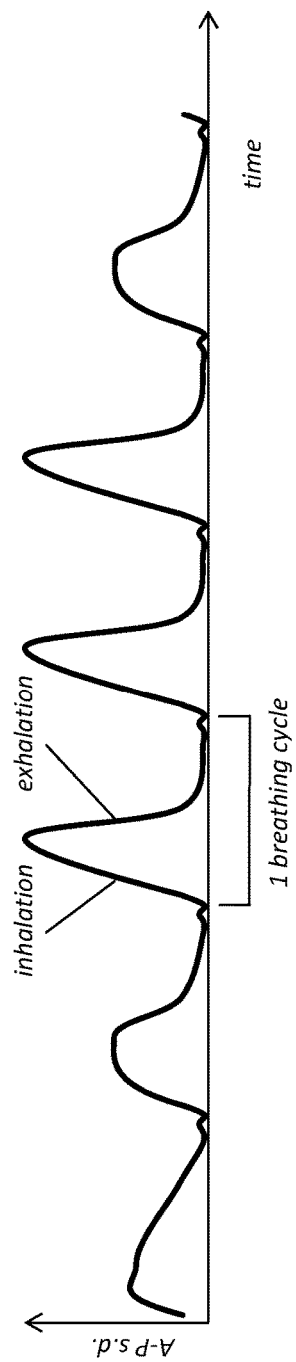
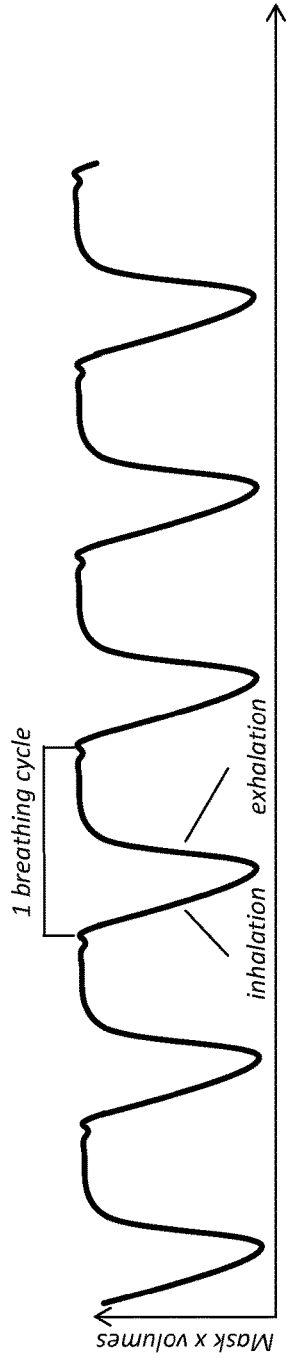
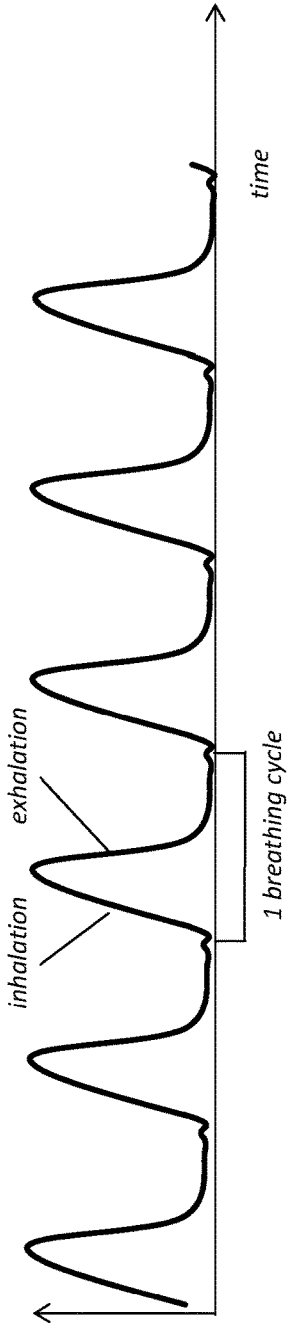
Fig. 3A
Fig. 3B
Fig. 3C

MOTION SIGNAL DERIVED FROM IMAGING DATA

CROSS REFERENCE TO RELATED APPLICATION

This application claims priority to U.S. Provisional Patent Application Ser. No. 62/652,942, filed on Apr. 5, 2018, which is incorporated herein by reference in its entirety.

TECHNOLOGY FIELD

The present invention relates generally to a method, system, and article of manufacture for deriving a motion signal from imaging data, for example, list mode data from a Positron Emission Tomography (PET) imaging acquisition with continuous bed motion (CBM).

BACKGROUND

Human motion, e.g., respiratory motion, is widely accepted as a cause of significant image degradation in PET imaging. Images can incur resolution loss from respiration-induced motion during PET image acquisition. In addition, in the combined PET-Computed Tomography (CT) imaging or combined PET-Magnetic resonance imaging (MRI) imaging, a resulting spatial mismatch between PET images and CT (or MRI) images can produce both localization inaccuracy and erroneous attenuation correction in PET.

Data-driven gating (DDG) methods estimate a motion signal, e.g., a respiratory curve, directly from acquired PET data, thereby eliminating the need for hardware-based respiratory monitoring devices and potentially facilitating a respiratory motion correction method which requires no operator interaction. However, existing DDG methods cannot robustly extend to multi-bed position PET imaging, because the arbitrary relationship between the polarity of the respiratory curve gradient (i.e., an increase of the signal amplitude or a decrease of the signal amplitude) and the direction of physical motion can unpredictably invert between bed positions. This renders these existing approaches inapplicable to oncological PET imaging that is typically acquired over more than one PET bed position.

SUMMARY

Embodiments provide a computer-implemented method of deriving a periodic motion signal from imaging data for continuous bed motion acquisition, the method comprising: acquiring a time series of three dimensional image volumes; estimating a first motion signal through a measurement of distribution of each three dimensional image volume; dividing the time-series of three dimensional image volumes into a plurality of axial sections overlapping each other by a predetermined amount, wherein each axial section has a predetermined length; performing a spectral analysis on each axial section to locate a plurality of three dimensional image volumes which are subject to a periodic motion; performing a phase optimization on each axial section to obtain a three dimensional mask; estimating a second motion signal through the three dimensional mask and the time-series of three dimensional image volumes, wherein the second motion signal has a consistent relationship between a polarity of a periodic motion signal gradient and a direction of the periodic motion; and estimating a final motion signal based on the first motion signal and the second motion signal.

Embodiments further provide a computer-implemented method, further comprising: identifying a dominant motion frequency of the first motion signal within a predefined frequency range; and performing the spectral analysis on each axial section using the dominant motion frequency.

Embodiments further provide a computer-implemented method, further comprising: applying a spatial filter to the time-series of three dimensional image volumes prior to dividing the time-series of three dimensional image volumes into a plurality of axial sections overlapping each other.

Embodiments further provide a computer-implemented method, further comprising: creating a phase weighted mask for each axial section in the spectral analysis; calculating an optimal phase-shift angle for each phase weighted mask to minimize a difference between overlapping sections of phase-weighted masks in the phase optimization; and combining all the phase-weighted masks to form the three dimensional mask.

Embodiments further provide a computer-implemented method, the step of estimating the second motion signal further comprising: multiplying the three dimensional mask by the time-series of three dimensional image volumes; and summing the resulting three dimensional image volumes to estimate the second motion signal.

Embodiments further provide a computer-implemented method, the step of estimating the final motion signal further comprising: determining the direction of the periodic motion associated with the final motion signal using the first motion signal.

Embodiments further provide a computer-implemented method, further comprising: normalizing the final motion signal; and obtaining an optimal gate to correct for temporal variations in an amplitude of the final motion signal, wherein the optimal gate is the smallest amplitude range covering a pre-determined fraction of acquisition time of the final motion signal.

Embodiments further provide a computer-implemented method, the step of normalizing the final motion signal further comprising: removing a frequency drift of the final motion signal by fitting a spline to the final motion signal; subtracting the spline from the final motion signal; normalizing the amplitude of the final motion signal; and performing baseline correction on the final motion signal.

Embodiments further provide a computer-implemented method, wherein the periodic motion is a respiratory motion or a cardiac motion.

Embodiments provide a system for deriving a periodic motion signal from imaging data for continuous bed motion acquisition, the system comprising: an imaging scanner for acquiring a time-series of three dimensional image volumes; and a computer system configured to: estimate a first motion signal through a measurement of distribution of each three dimensional image volume; apply a spatial filter to the time-series of three dimensional image volumes, thereby yielding a plurality of filtered three dimensional image volumes; divide the filtered three dimensional image volumes into a plurality of axial sections overlapping each other by a predetermined amount, wherein each axial section has a predetermined length; perform a spectral analysis on each axial section to locate a plurality of three dimensional image volumes which are subject to a periodic motion; perform a phase optimization on each axial section to obtain a three dimensional mask; estimate a second motion signal through the three dimensional mask and the time-series of three dimensional image volumes, wherein the second motion signal has a consistent relationship between a polarity of a periodic motion signal gradient and a direction of the periodic motion; and estimate a final motion signal based on the first motion signal and the second motion signal, wherein the direction of the periodic motion associated with the final motion signal is determined by the first motion signal.

Embodiments further provide a system for deriving a periodic motion signal from imaging data for continuous bed motion acquisition, the computer system is further configured to: identify a dominant motion frequency of the first motion signal within a predefined frequency range; and perform the spectral analysis on each axial section using the dominant motion frequency.

Embodiments further provide a system for deriving a periodic motion signal from imaging data for continuous bed motion acquisition, the computer system is further configured to: create a phase weighted mask for each axial section in the spectral analysis; calculate an optimal phase-shift angle for each phase weighted mask to minimize a difference between overlapping sections of phase-weighted masks in the phase optimization; and combine all the phase-weighted masks to form the three dimensional mask.

Embodiments further provide a system for deriving a periodic motion signal from imaging data for continuous bed motion acquisition, the computer system is further configured to: multiply the three dimensional mask by the filtered three dimensional image volumes; and sum the resulting three dimensional image volumes to estimate the second motion signal.

Embodiments further provide a system for deriving a periodic motion signal from imaging data for continuous bed motion acquisition, the computer system is further configured to: normalize the final motion signal; and obtain an optimal gate to correct for temporal variations in an amplitude of the final motion signal, wherein the optimal gate is the smallest amplitude range covering a pre-determined fraction of acquisition time of the final motion signal.

Embodiments further provide a system for deriving a periodic motion signal from imaging data for continuous bed motion acquisition, the computer system is further configured to: remove a frequency drift of the final motion signal by fitting a spline to the final motion signal; subtract the spline from the final motion signal; normalize the amplitude of the final motion signal; and perform baseline correction on the final motion signal.

Embodiments provide an article of manufacture for deriving a respiratory signal from imaging data for continuous bed motion acquisition, the article of manufacture comprising a non-transitory, tangible computer-readable medium holding computer-executable instructions for performing a method comprising: acquiring a time-series of three dimensional image volumes; estimating a first respiratory signal through a measurement of distribution of each three dimensional image volume; applying a spatial filter to the time-series of three dimensional image volumes, thereby yielding a plurality of filtered three dimensional image volumes; dividing the filtered three dimensional image volumes into a plurality of axial sections overlapping each other by a predetermined amount, wherein each axial section has a predetermined length; performing a spectral analysis on each axial section to locate a plurality of three dimensional image volumes which are subject to a respiratory motion; performing a phase optimization on each axial section to obtain a three dimensional mask; estimating a second respiratory signal through the three dimensional mask and the time-series of three dimensional image volumes, wherein the second respiratory signal has a consistent relationship between a polarity of a respiratory signal gradient and a direction of the respiratory motion; and estimating a final respiratory signal based on the first respiratory signal and the second respiratory signal.

Embodiments further provide an article of manufacture for deriving a respiratory signal from imaging data for continuous bed motion acquisition, the method further comprising: multiplying the three dimensional mask by the filtered three dimensional image volumes; and summing the resulting three dimensional image volumes to estimate the second respiratory signal.

Embodiments further provide an article of manufacture for deriving a respiratory signal from imaging data for continuous bed motion acquisition, the method further comprising: normalizing the final respiratory signal; and obtaining an optimal gate to correct for temporal variations in an amplitude of the final respiratory signal, wherein the optimal gate is the smallest amplitude range covering a pre-determined fraction of acquisition time of the final respiratory signal.

Embodiments further provide an article of manufacture for deriving a respiratory signal from imaging data for continuous bed motion acquisition, the method further comprising: removing a frequency drift of the final respiratory signal by fitting a spline to the final respiratory signal; subtracting the spline from the final respiratory signal; normalizing the amplitude of the final respiratory signal; and performing baseline correction on the final respiratory signal.

Embodiments further provide an article of manufacture for deriving a respiratory signal from imaging data for continuous bed motion acquisition, wherein at least two axial sections have different lengths, and at least two pairs of adjacent axial sections overlap by different amounts.

Embodiments further provide a method of deriving a motion signal from imaging data, comprising: acquiring a time-series of three dimensional image volumes; generating the motion signal based on the time-series of three dimensional image volumes; and obtaining an optimal gate to correct for temporal variations in an amplitude of the motion signal, wherein the optimal gate is the smallest amplitude range covering a pre-determined fraction of acquisition time of the motion signal.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIGS. 3A-3C illustrate three diagrams of a motion signal estimated in different steps of the method of FIG. 2, according to some embodiments described herein;

DETAILED DESCRIPTION OF ILLUSTRATIVE EMBODIMENTS

The following disclosure describes several embodiments directed at a method, system, and article of manufacture related to deriving a motion signal from imaging data (e.g., PET imaging data, MRI imaging data, CT imaging data, single-photon emission computerized tomography (SPECT) imaging data, or other imaging modality data). More particularly, the method, system, and article of manufacture exploits the continuous-bed-motion (CBM) acquisition mode to estimate a periodic motion signal (e.g., a respiratory signal, a cardiac motion signal) directly from acquired PET data of a whole-body PET, with the polarity of a motion signal gradient consistent with the direction of motion (e.g., breathing in or breathing out).

According to various embodiments of the present invention, described in more detail below, acquisition data in list mode format is converted to a time series of spatially filtered, time-of-flight (ToF) volumes, and an initial estimate of the respiratory signal (i.e., the first respiratory signal) is obtained by calculating the time-varying anterior-posterior (AP) displacement in the Y direction (i.e., anterior-posterior direction of human anatomy). The full acquisition range is then divided into a series of overlapping short axial sections along the superior-inferior direction. The series of axial sections are subject to a spectral analysis, initialized with a dominant respiratory frequency obtained from the first respiratory signal. In the spectral analysis, a phase optimization process is used to combine the axial sections, and produce a second estimated respiratory signal having a consistent relationship between the physical direction of motion and the polarity of respiratory signal gradient throughout the acquisition range. A final estimated respiratory signal is then obtained with a definite relationship between the polarity of the signal gradient and the direction of motion identified by the first respiratory signal.

In an embodiment, the final estimated respiratory signal is normalized and an adaptive gating methodology is used to correct for temporal variations in the shape and amplitude of the respiratory signal and produce a gated respiratory signal with axially uniform noises.

The method, system, and article of manufacture combine two independently-derived respiratory signals (i.e., the first respiratory signal and the second respiratory signal), separate the acquisition into overlapping axial sections, and ensure a consistent relationship between the polarity of a final respiratory signal gradient and the direction of motion throughout an image acquisition.

Figure 1:
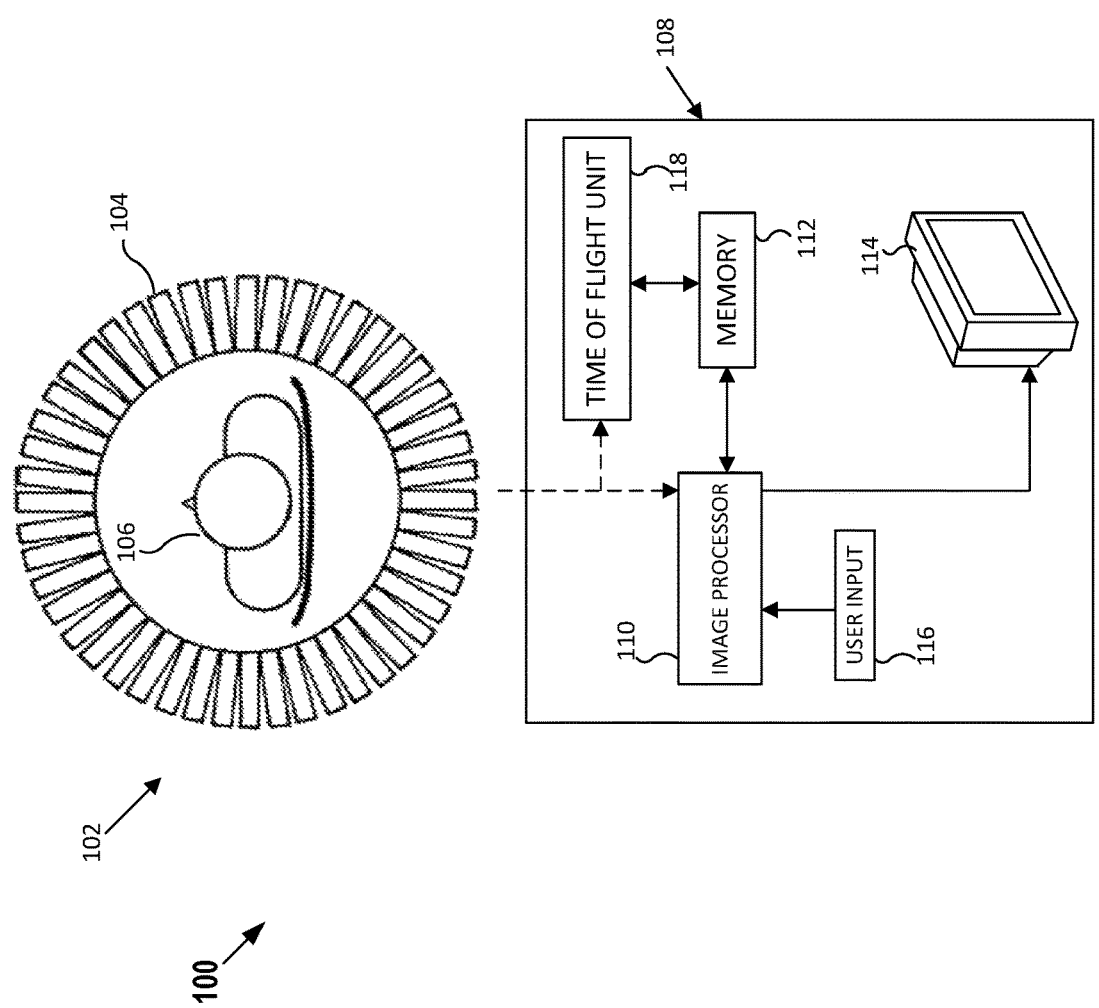
FIG. 1 shows a system for a PET scanner, as used by some embodiments described herein.

FIG. 1 depicts an example PET system 100, as used by some embodiments described herein. The PET system 100 may generally have an imaging scanner 102 and a PET processing system 108. The imaging scanner 102 includes a plurality of detectors 104 arranged in a circular manner about a subject 106, e.g., a patient. The detectors 104 are arranged on the inside surface of a cylindrical structure, and the subject 106 is placed within the cylinder so that the detectors 104 surround the subject 106 on all sides. Each of the detectors 104 may further be rotatable around the subject 106. While the detectors 104 shown herein are rectangular in shape, those skilled in the art will recognize that the detectors 104 may be in any shape without departing from the scope of this disclosure.

To obtain a PET image of the subject 106, a radiopharmaceutical is first injected into the subject 106. The radiopharmaceutical contains a targeting aspect which interacts with a molecule or process of interest within the patient's body, such as glucose metabolism. The radiopharmaceutical also contains a positron-emitting radionuclide. An emitted positron will collide with an electron from a nearby atom, and the positron and the electron annihilate. As a result of the annihilation, two different photons are emitted in substantially opposite directions along a line of response. The photons both travel at the substantially same speed. The detectors 104 record these photons, along with PET imaging data associated with the photons, such as the time each photon is detected.

The PET imaging scanner 102 passes the PET imaging data recorded by the detectors 104 on to a PET processing system 108. In this embodiment, the PET imaging scanner 102 and the PET processing system 108 are shown and described herein as being separate systems. In another embodiment, the PET imaging scanner 102 and the PET processing system 108 can be part of a single, unitary system. The PET imaging data is sent to an image processor 110, and then stored in a memory 112 in list mode format. The image processor 110 processes the PET imaging data, and generates images of the imaged subject 106. The resulting images can be shown on a display 114 associated with the image processor 110. A user input 116, such as a keyboard and/or mouse device may be provided for a user to manipulate the resulting images shown on the display 114, e.g., image zooming, image rotation, etc.

As illustrated in FIG. 1, the PET processing system 108 further includes a time of flight (ToF) unit 118, configured to calculate a position along each line of response where the annihilation occurred, thus increasing the resolution of the PET image reconstruction. The precise time that each of the coincident photons is detected by the detectors 104 is recorded. Since the closer photon will arrive at its detector first, the difference in arrival times helps pin down the location of the annihilation event along the line of response. With the PET system 100 as illustrated in FIG. 1, a ToF-PET scan is performed.

Figure 2:
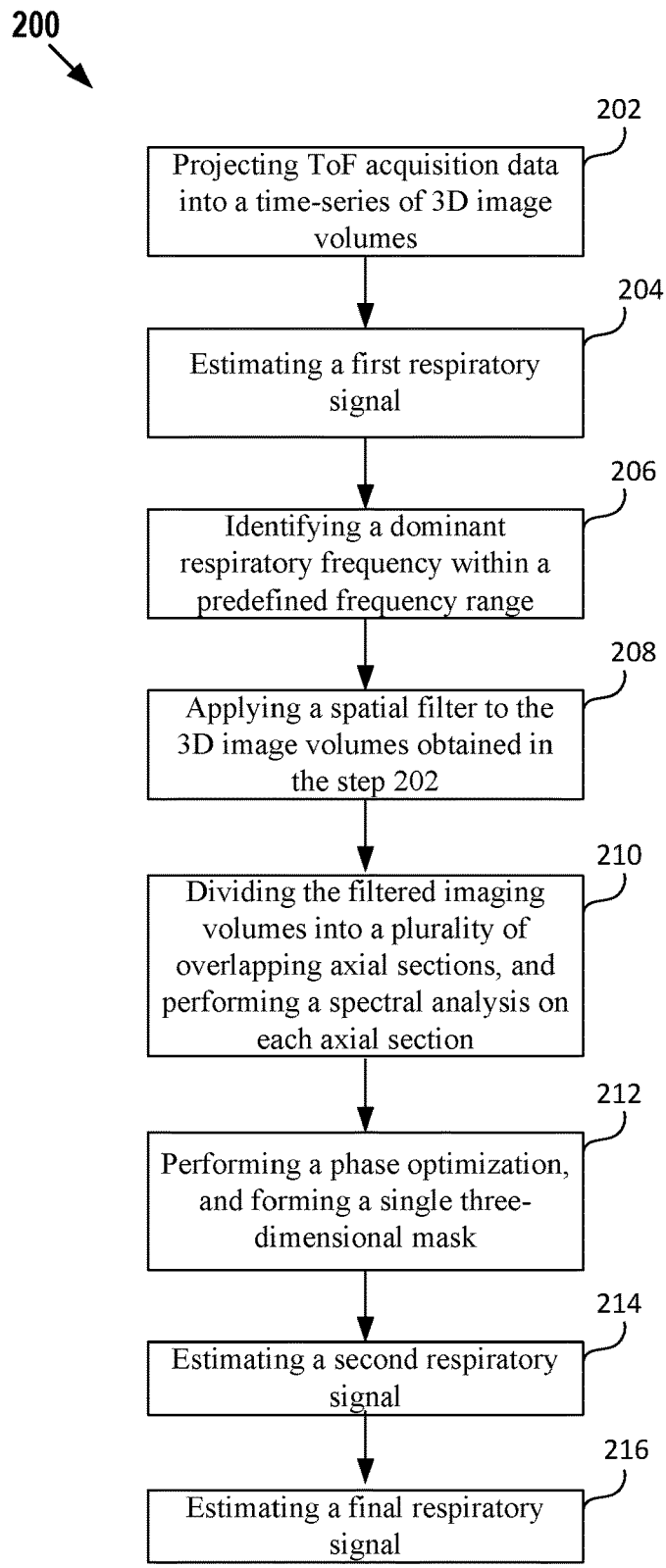
FIG. 2 illustrates a flowchart of a method of deriving a motion signal from imaging data, according to some embodiments described herein.

FIG. 2 illustrates a flowchart of a method of deriving an estimated respiratory signal from acquisition data, according to some embodiments described herein. It should be noted that, although the PET system 100 is used as example for implementing the method described herein, the method can be readily adapted to other imaging modalities including, without limitation SPECT, MRI, and CT.

At step 202, ToF acquisition data is projected into a time-series of 3D image volumes, and each 3D image volume is rendered with the Cartesian coordinate system (i.e., (x,y,z)).

As is generally understood in the art, in PET imaging, the imaging scanner 102 detects pairs of gamma rays emitted indirectly by a positron-emitting radionuclide. When a positron is annihilated by an electron, two gamma photons are simultaneously produced and travel in approximately opposite directions. The gamma photons are detected by a pair of oppositely disposed radiation detectors 104 that produce a signal in response to the interaction of the gamma photons with a scintillation crystal.

The ToF unit 118 measures the difference Δt between the detection times of the two gamma photons arising from a positron annihilation event. This measurement allows the annihilation event to be localized along line(s)-of-response (LOR). This approximate localization is effective in reducing the random coincidence rate and in improving the signal-to-noise ratio (SNR) of the signal, especially when imaging large objects. Thus, in ToF-PET, the "ToF" coordinate, Δt, is stored together with the location of the two crystals that detect the photon pair. The ToF PET data, including Δt, and the location, is acquired and stored in list mode format. With list mode processing, digitized signals are coded with "time marks" as they are received in sequence and stored as individual events as they occur. The ToF PET data is projected into a time-series of 3D image volumes having Cartesian coordinates (also called "Cartesian volumes"), by placing each LOR into a single voxel located at the center of the ToF window.

At step 204, referring to FIG. 3A, a first respiratory signal is estimated. The measurement of distribution (e.g., standard deviation, full-with-half maximum measurement, etc.) of each 3D Cartesian volume in the Y direction (anterior-posterior axis) is calculated, and all the measurements of distribution of Cartesian volumes are utilized to generate a time curve (a curve of distribution versus time, e.g., a curve of standard deviation versus time), i.e., the first respiratory signal. This time curve provides an estimate of the subject's respiration while the PET data was being acquired. The measurement of distribution can be any measurement that quantifies the amount of variation or dispersion of a set of data values. The measurement of distribution can be standard deviation, or full-with-half maximum measurement, etc. Equation 1 illustrates the standard deviations of Cartesian volumes:

$$r_{sd(t)} = s.d. \left\{ \sum^{Z} \sum^{X} P \right\}$$ (Equation 1)

In the Equation 1, $r_{sd(t)}$ is the first respiratory signal; "P" is a 3D Cartesian volume at time t; "s.d." is a standard deviation operator. The standard deviations of all the Cartesian volumes reflect activity distribution in the Y direction (the anterior-posterior axis), for example, when the subject 106 (e.g., a patient) breathes in, the abdomen expands and the standard deviation is increased, while when the subject 106 breathes out, the abdomen contracts and the standard deviation is decreased. Thus, the polarity of the first respiratory signal gradient can clearly indicate the direction of abdomen motion (i.e., breathing in or breathing out). However, the first respiratory signal lacks accuracy, especially for certain anatomical regions. For example, the abdominal wall is subject to more anterior-posterior motion during respiration than, for instance, the chest. Thus, the first respiratory signal may lack accuracy for chest region.

At step 206, a Fast Fourier Transform (FFT) is performed to divide the first respiratory signal into its frequency components, a dominant respiratory frequency is then identified by determining a peak of the spectral magnitude of the frequency components within a predefined frequency range and within a predefined temporal range. Equation 2 illustrates identification of a dominant respiratory frequency of the first respiratory signal:

$$\operatorname*{argmax}_{f \in [f1,f2]} |R_{sd}|$$ (Equation 2)

In the Equation 2, $R_{sd}$ is FFT of the first respiratory signal; f1 and f2 respectively define a starting frequency and an ending frequency of a frequency range. The frequency range should be wide enough to cover the dominant respiratory frequency. An example frequency range is 0.1 Hz to 0.4 Hz, which covers the typical dominant respiratory frequency of around 0.2 Hz. In another embodiment, if the motion signal is a cardiac signal, then the example frequency range can be set, e.g., as 0.8 Hz to 1.2 Hz, because the dominant cardiac frequency is around 1 Hz. Thus, the frequency range can be set to look for a specific type of periodic motion, e.g., a respiratory motion, or a cardiac motion, etc.

At step 208, a spatial filter is applied to the 3D Cartesian volumes obtained in the step 202. In general, the Cartesian volumes generated during the step 202 are very noisy. A spatial filter, e.g., a 3D Gaussian filter, is thus applied to the Cartesian volumes to reduce noises. After filtering, the filtered Cartesian volumes are Fast Fourier transformed (FFT) in the temporal domain.

At step 210, the filtered Cartesian volumes are divided into a plurality of axial sections along Z direction (i.e., superior-inferior axis), each axial section having a predetermined length. The axial sections overlap by a predetermined amount, e.g., 90%. A spectral analysis is then performed on each individual axial section, to locate specific acquisition data which is subject to respiratory motion. In an embodiment, each axial section has the same length, e.g., 10 cm. The length of each axial section can be adjusted based on an axial field of view of the PET imaging scanner 102, a bed speed, and a type of radiopharmaceutical. In another embodiment, lengths of axial sections can be different from each other, instead of a same length. In an embodiment, the overlap amounts can be different from each other, instead of a same amount. The length of axial sections and the overlap amount can be changed for different acquisitions and different scanners.

As is generally understood in the art, the spectral analysis on a signal includes applying a window that selects a spectral segment of the signal for analysis. One example method for performing the spectral analysis is described in Schleyer et al. PMB 2009 "Retrospective Data-Driven Respiratory Gating for PET/CT." However, it should be understood that other similar techniques for performing spectral analysis generally known in the art may be used. The estimated dominant respiratory frequency obtained in the step 206 is used to specify the center of the window. The spectral analysis thus creates a window around the dominant respiratory frequency estimated in the step 206. In the spectral analysis, a phase weighted mask is created for each axial section, to identify voxels that are subject to a respiratory motion. Thus, all the phase weighted masks allow a further analysis to be performed only on the voxels in the volumes that are moving. Phase weighting of each mask is used to separate regions of each mask according to different directions of motion (i.e., separating what is moving "up" from what is moving "down"). For example, if the patient breathes in, the direction of the motion is moving up, while if the patient breathes out, the direction of the motion is moving down. While separation of regions corresponding to different directions of motion is achieved, the absolute direction of motion is not known. In addition, the relationship between the phase weights and the direction of motion can be different at different axial locations due to an irregular nature of the motion and properties of FFT.

At step 212, a phase optimization is performed to ensure that there is a consistent relationship between the phase weights and the direction of motion at each of the phase weighted masks generated at the step 210, and further ensure a consistent relationship between a polarity of the respiratory signal gradient and the direction of motion for all individual axial sections. In this step, an optimal phase-shift angle is calculated for each phase weighted mask generated in the step 210 (i.e., an optimal phase-shift angle is calculated for each axial section). The phase weight at each (x,y,z) location in a mask, i.e., $\phi_{xyz}$, is offset by the optimal phase-shift angle $\Phi_{opt}$ to produce a corrected phase weight $\phi'_{xyz}$, as illustrated in Equation 3.

$$\phi'_{xyz} = \phi_{xyz} - \Phi_{opt} \qquad \text{(Equation 3)}$$

The optimal phase-shift angle $\Phi_{opt}$, for each axial range, is defined as an angle that minimizes the difference between the overlapping sections of the phase-weighted masks (because axial sections overlap, thus the phase-weighted masks also overlap). Thus, the optimal phase-shift angle ensures that a consistent phase weighting is applied to all the different axial regions. This helps prevent the spontaneous phase flipping that may occur at different axial locations. Each optimal phase-shift angle can be found through an exhaustive search or a heuristic search. After the phase of each axial section is corrected or optimized, all phase-weighted masks are combined into a single three-dimensional mask, so that a periodic motion during the entire axial scan can be identified.

The phase optimization step is an in-place operation (i.e., the phase-shift of a given axial range is implemented before progressing to the next range), and thus, the result of the phase optimization step depends on an axial starting point. Therefore, in one embodiment, the axial starting point is determined as an axial location where the largest mean spectral magnitude within the frequency window [f1, f2] was found in the first respiratory signal. In another embodiment, the axial starting point is determined as the center of the overall axial range of the acquisition.

At step 214, the single three-dimensional mask is multiplied by the filtered Cartesian volumes of the step 208, and the resulting Cartesian volumes are summed together to produce a second estimated respiratory signal (as shown in FIG. 3B). The single three-dimensional mask can extract Cartesian volumes that are subject to a respiratory motion, thus the resulting Cartesian volumes indicative of displacement of the whole patient body can be used to generate the second estimated respiratory signal. Due to the single three-dimensional mask constructed from the phase-optimized individual masks, the resulting Cartesian volumes have a consistent relationship between the polarity of respiratory motion gradient and the direction of respiratory motion across the entire axial field of view. For example, across the entire axial field of view, a positive increase in motion signal results from inspiration (breathing in), while a negative decrease in motion signal results from expiration (breathing out). For another example, on the contrary, a positive increase in motion signal results from expiration, while a negative decrease in motion signal results from inspiration. Across the entire axial field of view, the relationship between the polarity of the motion signal gradient and the direction of the motion signal is consistent.

At step 216, referring to FIG. 3C, a final estimated respiratory signal is generated based on the first estimated respiratory signal generated at the step 204 and the second estimated respiratory signal generated at the step 214. This final estimated respiratory signal has a consistent and absolute relationship between the polarity of respiratory motion gradient and the physical direction of motion for the entire length of the scan. The first respiratory signal from the step 204 is obtained by calculating standard deviation of each Cartesian volume in the Y direction (the anterior-posterior axis), thus the first respiratory signal can be used to decide the absolute direction of the motion of the patient. Accordingly, the first respiratory signal from the step 204 and the second estimated respiratory signal from the step 214 are used together to derive the final estimated respiratory signal. The absolute motion direction of the final estimated respiratory signal can be obtained from the first respiratory signal, while the consistent relationship between the polarity of the signal gradient and the physical direction of motion can be obtained from the second more accurate respiratory signal.

Figure 4:
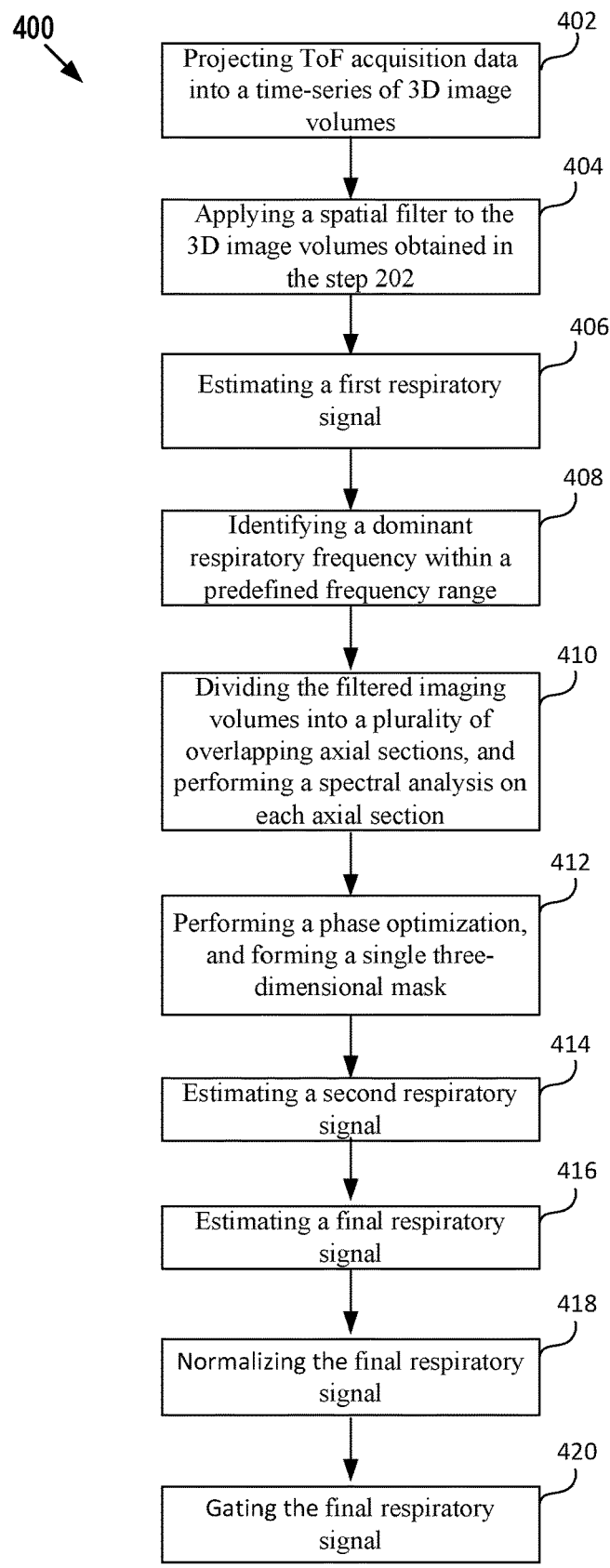
FIG. 4 illustrates another flowchart of a method of deriving a motion signal from imaging data, according to some embodiments described herein.

FIG. 4 illustrates another flowchart of a method 400 of deriving an estimated respiratory signal from acquisition data, according to some embodiments described herein. The steps 402-416 are similar to the steps 202-216 of FIG. 2. The only difference is that the step of applying a spatial filter (step 404, corresponding to the step 208 of FIG. 2) is performed prior to the step of estimating a first respiratory signal (step 406, corresponding to the step 204 of FIG. 2).

Figure 5A:
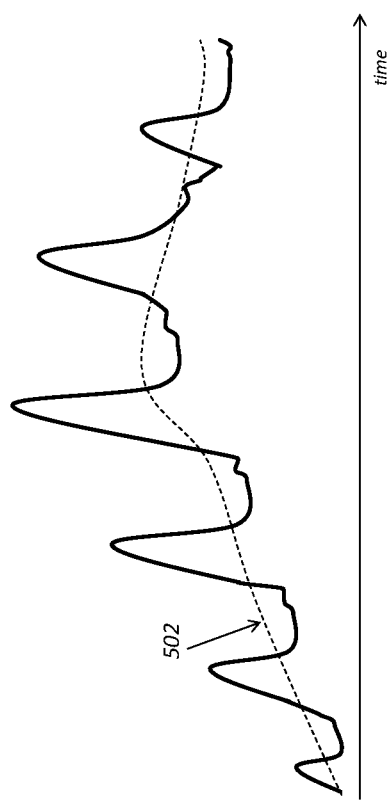
FIGS. 5A and 5B illustrate two diagrams of normalizing a motion signal, according to some embodiments described herein.
Figure 5B:
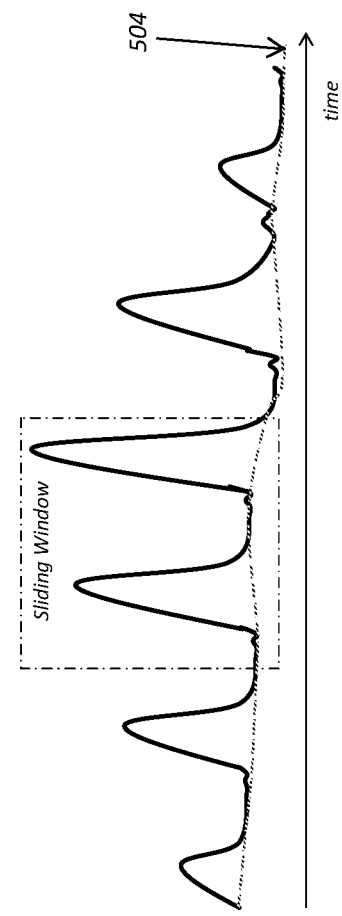

At step 418, referring to FIGS. 5A and 5B, a curve normalization is performed on the final estimated respiratory signal for the later gating step 420. The final respiratory signal is estimated from different axial sections of the patient body as the patient moves through the scanner, and there are different intensities of activity and different amplitudes of motion for each anatomical region or each axial section of the patient. Therefore, the relationship between the amplitude of the respiratory signal and amplitude of the breathing is arbitrary in scale at different axial sections, and thus a curve normalization is further performed on the final estimated respiratory signal. Referring to FIGS. 5A and 5B, the normalization approach is performed in four steps. During the first normalization step, referring to FIG. 5A, low frequency drift of the final estimated respiratory signal is removed by fitting a spline 502 to the final estimated respiratory signal. In the second normalization step, the spline 520 is subtracted from the final estimated respiratory signal, as illustrated in Equation 4.

$$r_{step2}(t) = r(t) - \text{spline}(t) \qquad \text{(Equation 4)}$$

In the Equation 4, $r_{step2}[t]$ is the curve generated by the second normalization step at a time point t.

During the third normalization step, referring to FIG. 5B, the amplitude of the final estimated respiratory signal is normalized. The final estimated respiratory signal is divided by a standard deviation within a sliding window (e.g., 90 seconds) of the final estimated respiratory signal, as illustrated in Equation 5.

$$r_{step3}[t] = \frac{r_{step2}[t]}{s.d.\{r_{step2}[t-w:t+w]\}} \qquad \text{(Equation 5)}$$

In the Equation 5, $r_{step3}[t]$ is the curve generated by the third normalization step at a time point t; $r_{step2}[t]$ is the curve generated by the second normalization step at a time point t; and s.d.$\{r_{step2}[t-w:t+w]\}$ is the standard deviation of the curve from the second normalization step in the time range [t−w, t+w], where 2*w defines the width of the sliding window.

Finally, during the fourth step, the minimum curve 504 of the final estimated respiratory signal is subtracted from the final estimated respiratory signal to baseline correct the final estimated respiratory signal, as illustrated in Equation 6.

$$r_{step4}[t] = r_{step3}[t] - \min\{r_{step3}[t-v:t+x]\} \quad \text{(Equation 6)}$$

In the Equation 6, $r_{step4}[t]$ is the curve generated by the fourth normalization step at a time point t, $r_{step3}[t]$ is the curve generated by the third normalization step at time-point t, and $\min\{r_{step3}[t-v:t+v]\}$ is the minimum of the curve from the third normalization step in the time range [t−v:t+v], where 2*v defines the width of a sliding window.

After normalization, the normalized final estimated respiratory signal is ready for gating. At step 420, an adaptive gating method is employed to correct for temporal variations in the amplitude of the respiratory signal (i.e., potential non-linear variations in the relationship between signal amplitude and physical motion amplitude). Specifically, a dynamic optimal gate is created to allow for intra-acquisition changes in both respiratory signal amplitude and a shape (i.e., unevenness of the respiratory signal curve due to different anatomical regions being imaged at different times during the acquisition). The optimal gate is defined as the smallest amplitude range which covers a pre-determined fraction (e.g., 35%) of acquisition time of the respiratory signal. In the smallest amplitude range of the respiratory curve, the patient spends as much acquisition time as possible while having a minimum motion. For example, the patient spends a majority of acquisition time on the expiration (e.g., 35%) while having minimum motion. The noises can be reduced if there is more acquisition time, while the blurring can be reduced if there is less motion (i.e., smaller amplitude range). The optimal gate is a trade-off between the more acquisition time and the less motion. The size of the time window (i.e., a pre-determined fraction of acquisition time) is an adjustable parameter.

Figure 6A:
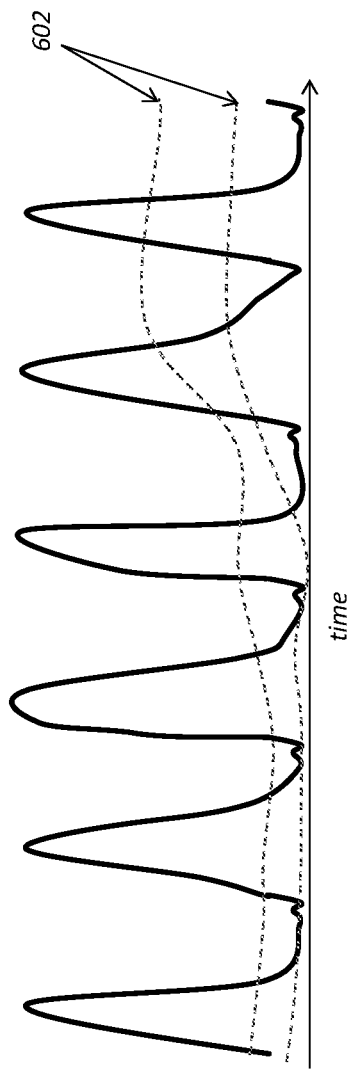
FIGS. 6A and 6B illustrate two diagrams of locating an optimal gate of a motion signal, according to some embodiments described herein.
Figure 6B:
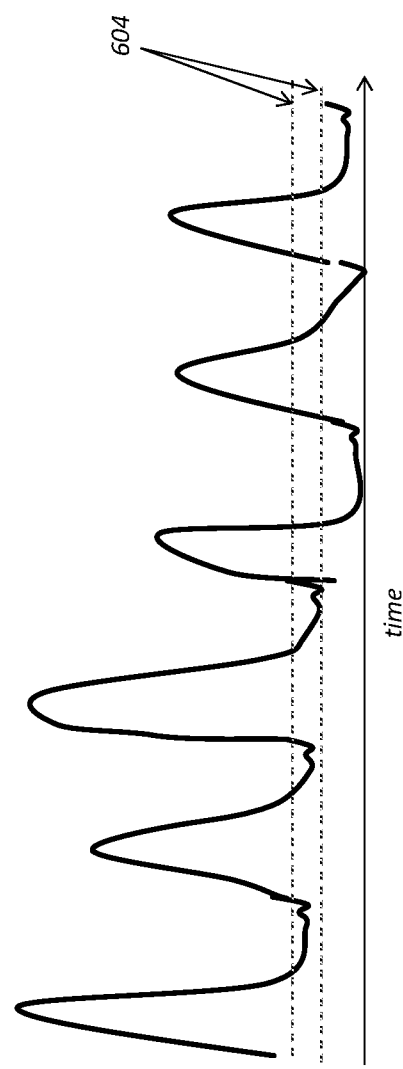

In an embodiment, referring to FIG. 6A, a temporally variant optimal amplitude range 602 is calculated using a sliding window (e.g., 90 seconds) approach. This temporally variant optimal amplitude range 602 can be directly used to gate the PET acquisition into a single optimal sinogram. In another embodiment, referring to FIG. 6B, the respiratory signal can be dynamically normalized using the temporally variant optimal amplitude range, and a single (i.e., static) amplitude range 604 can then be used to gate the acquisition. The single (i.e., static) amplitude range 604 defines an optimal gate for the entire duration of the acquisition.

Further, motion correction can be performed based on the optimal gate and the final respiratory signal estimated at step 216, and then a whole body PET image with motion correction is reconstructed.

The method, system, and article of manufacture of this disclosure require no physical motion monitoring devices, and apply data-driven gating to whole body PET acquired with continuous bed motion. A consistent relationship between the polarity of the respiratory signal gradient and the direction of motion is provided throughout the image acquisition.

Figure 7:
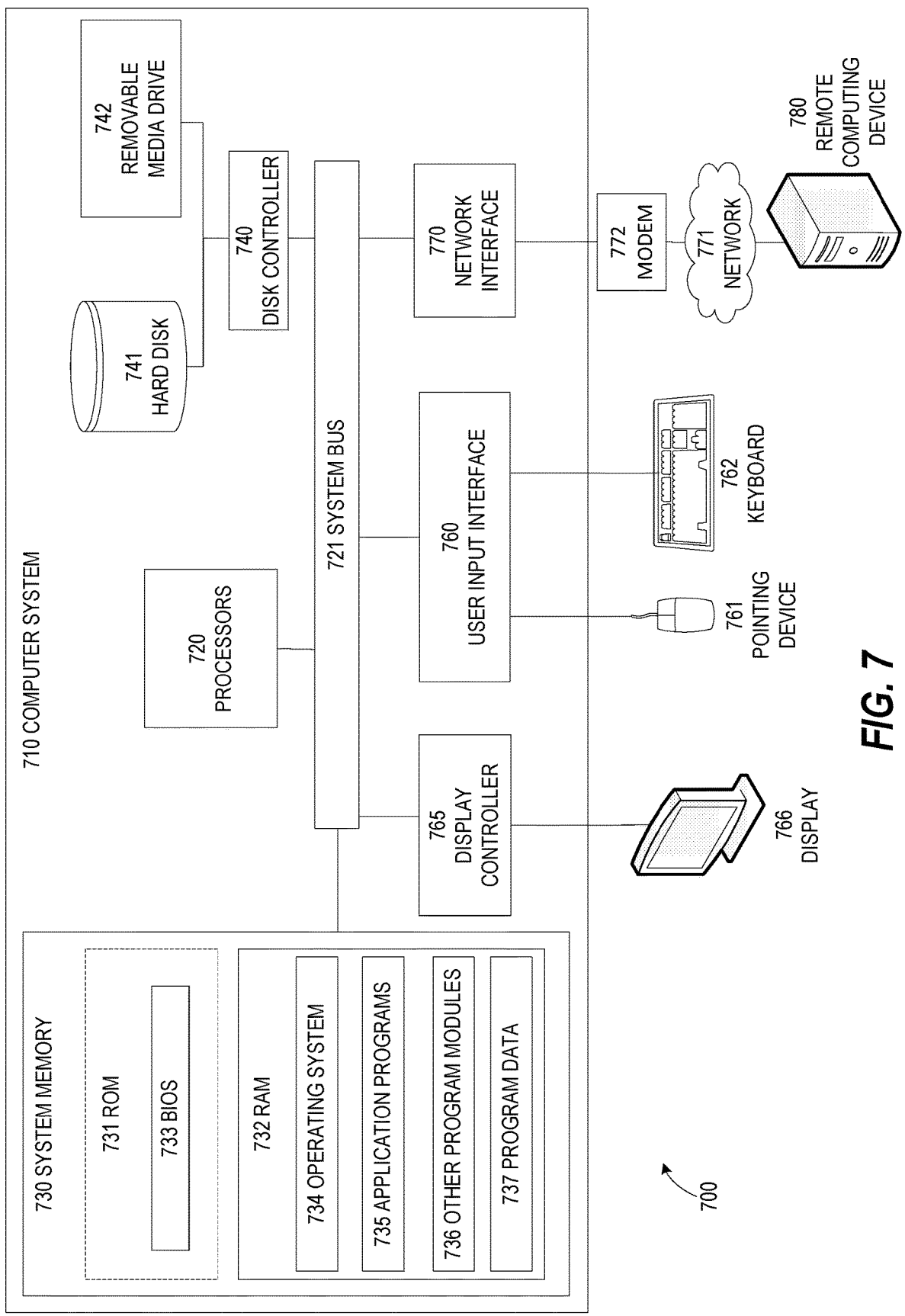
FIG. 7 illustrates an exemplary computing environment within which embodiments of the invention may be implemented.

FIG. 7 illustrates an exemplary computing environment 700 within which embodiments of the invention may be implemented. For example, this computing environment 700 may be used to implement a method of deriving a motion signal from imaging data, as illustrated in FIGS. 2 and 4. In some embodiments, the computing environment 700 may be used to implement one or more of the components illustrated in the system 100 of FIG. 1. The computing environment 700 may include computer system 710, which is one example of a computing system upon which embodiments of the invention may be implemented. Computers and computing environments, such as computer system 710 and computing environment 700, are known to those of skill in the art and thus are described briefly here.

As shown in FIG. 7, the computer system 710 may include a communication mechanism such as a bus 721 or other communication mechanism for communicating information within the computer system 710. The computer system 710 further includes one or more processors 720 coupled with the bus 721 for processing the information. The processors 720 may include one or more central processing units (CPUs), graphical processing units (GPUs), or any other processor known in the art.

The computer system 710 also includes a system memory 730 coupled to the bus 721 for storing information and instructions to be executed by processors 720. The system memory 730 may include computer readable storage media in the form of volatile and/or nonvolatile memory, such as read only memory (ROM) 731 and/or random access memory (RAM) 732. The system memory RAM 732 may include other dynamic storage device(s) (e.g., dynamic RAM, static RAM, and synchronous DRAM). The system memory ROM 731 may include other static storage device (s) (e.g., programmable ROM, erasable PROM, and electrically erasable PROM). In addition, the system memory 730 may be used for storing temporary variables or other intermediate information during the execution of instructions by the processors 720. A basic input/output system (BIOS) 733 containing the basic routines that help to transfer information between elements within computer system 710, such as during start-up, may be stored in ROM 731. RAM 732 may contain data and/or program modules that are immediately accessible to and/or presently being operated on by the processors 720. System memory 730 may additionally include, for example, operating system 734, application programs 735, other program modules 736 and program data 737.

The computer system 710 also includes a disk controller 740 coupled to the bus 721 to control one or more storage devices for storing information and instructions, such as a hard disk 741 and a removable media drive 742 (e.g., floppy disk drive, compact disc drive, tape drive, and/or solid state drive). The storage devices may be added to the computer system 710 using an appropriate device interface (e.g., a small computer system interface (SCSI), integrated device electronics (IDE), Universal Serial Bus (USB), or FireWire).

The computer system 710 may also include a display controller 765 coupled to the bus 721 to control a display 766, such as a cathode ray tube (CRT) or liquid crystal display (LCD), for displaying information to a computer user. The computer system includes an input interface 760 and one or more input devices, such as a keyboard 762 and a pointing device 761, for interacting with a computer user and providing information to the processors 720. The pointing device 761, for example, may be a mouse, a trackball, or a pointing stick for communicating direction information and command selections to the processor 720 and for controlling cursor movement on the display 766. The display 766 may provide a touch screen interface which allows input to supplement or replace the communication of direction information and command selections by the pointing device 761.

The computer system 710 may perform a portion of or all of the processing steps of embodiments of the invention in response to the processors 720 executing one or more sequences of one or more instructions contained in a memory, such as the system memory 730. Such instructions may be read into the system memory 730 from another computer readable medium, such as a hard disk 741 or a removable media drive 742. The hard disk 741 may contain one or more data stores and data files used by embodiments of the present invention. Data store contents and data files may be encrypted to improve security. The processors 720 may also be employed in a multi-processing arrangement to execute the one or more sequences of instructions contained in system memory 730. In alternative embodiments, hard-wired circuitry may be used in place of or in combination with software instructions. Thus, embodiments are not limited to any specific combination of hardware circuitry and software.

As stated above, the computer system 710 may include at least one computer readable medium or memory for holding instructions programmed according to embodiments of the invention and for containing data structures, tables, records, or other data described herein. The term "computer readable medium" as used herein refers to any medium that participates in providing instructions to the processors 720 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 741 or removable media drive 742. Non-limiting examples of volatile media include dynamic memory, such as system memory 730. Non-limiting examples of transmission media include coaxial cables, copper wire, and fiber optics, including the wires that make up the bus 721. Transmission media may also take the form of acoustic or light waves, such as those generated during radio wave and infrared data communications.

The computing environment 700 may further include the computer system 710 operating in a networked environment using logical connections to one or more remote computers, such as remote computer 780. Remote computer 780 may be a personal computer (laptop or desktop), a mobile device, a server, a router, a network PC, a peer device or other common network node, and typically includes many or all of the elements described above relative to computer system 710. When used in a networking environment, computer system 710 may include modem 772 for establishing communications over a network 771, such as the Internet. Modem 772 may be connected to bus 721 via user network interface 770, or via another appropriate mechanism.

Network 771 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 710 and other computers (e.g., remote computer 780). The network 771 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 771.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. § 112 (f), unless the element is expressly recited using the phrase "means for."

We claim:

1. A computer-implemented method of deriving a periodic motion signal from imaging data for continuous bed motion acquisition, the method comprising:
   acquiring a time series of three dimensional image volumes;
   estimating a first motion signal through a measurement of distribution of each three dimensional image volumes;
   dividing the time-series of three dimensional image volumes into a plurality of axial sections overlapping each other by a predetermined amount, wherein each axial section has a predetermined length;
   performing a spectral analysis on each axial section to locate a plurality of three dimensional image volumes which are subject to a periodic motion;
   performing a phase optimization on each axial section to obtain a three dimensional mask;
   estimating a second motion signal through the three dimensional mask and the time-series of three dimensional image volumes, wherein the second motion signal has a consistent relationship between a polarity of a periodic motion signal gradient and a direction of the periodic motion; and
   estimating a final motion signal based on the first motion signal and the second motion signal.

2. The method of claim 1, further comprising:
   identifying a dominant motion frequency of the first motion signal within a predefined frequency range; and
   performing the spectral analysis on each axial section using the dominant motion frequency.

3. The method of claim 1, further comprising:
   applying a spatial filter to the time-series of three dimensional image volumes prior to dividing the time-series of three dimensional image volumes into a plurality of axial sections overlapping each other.

4. The method of claim 1, further comprising:
   creating a phase weighted mask for each axial section in the spectral analysis;
   calculating an optimal phase-shift angle for each phase weighted mask to minimize a difference between overlapping sections of phase-weighted masks in the phase optimization; and
   combining all the phase-weighted masks to form the three dimensional mask.

5. The method of claim 1, the step of estimating the second motion signal further comprising:
   multiplying the three dimensional mask by the time-series of three dimensional image volumes; and
   summing the resulting three dimensional image volumes to estimate the second motion signal.

6. The method of claim 1, the step of estimating the final motion signal further comprising:
   determining the direction of the periodic motion associated with the final motion signal using the first motion signal.

7. The method of claim 1, further comprising:
   normalizing the final motion signal; and
   obtaining an optimal gate to correct for temporal variations in an amplitude of the final motion signal, wherein the optimal gate is the smallest amplitude range covering a pre-determined fraction of acquisition time of the final motion signal.

8. The method of claim 7, the step of normalizing the final motion signal further comprising:
   removing a frequency drift of the final motion signal by fitting a spline to the final motion signal;
   subtracting the spline from the final motion signal;
   normalizing the amplitude of the final motion signal; and
   performing baseline correction on the final motion signal.

9. The method of claim 1, wherein the periodic motion is a respiratory motion or a cardiac motion.

10. A system for deriving a periodic motion signal from imaging data for continuous bed motion acquisition, the system comprising:
    an imaging scanner for acquiring a time-series of three dimensional image volumes; and
    a computer system configured to:
       estimate a first motion signal through a measurement of distribution of each three dimensional image volumes;
       apply a spatial filter to the time-series of three dimensional image volumes, thereby yielding a plurality of filtered three dimensional image volumes;
       divide the filtered three dimensional image volumes into a plurality of axial sections overlapping each other by a predetermined amount, wherein each axial section has a predetermined length;
       perform a spectral analysis on each axial section to locate a plurality of three dimensional image volumes which are subject to a periodic motion;
       perform a phase optimization on each axial section to obtain a three dimensional mask;
       estimate a second motion signal through the three dimensional mask and the time-series of three dimensional image volumes, wherein the second motion signal has a consistent relationship between a polarity of a periodic motion signal gradient and a direction of the periodic motion; and
       estimate a final motion signal based on the first motion signal and the second motion signal, wherein the direction of the periodic motion associated with the final motion signal is determined by the first motion signal.

11. The system of claim 10, the computer system is further configured to:
    identify a dominant motion frequency of the first motion signal within a predefined frequency range; and
    perform the spectral analysis on each axial section using the dominant motion frequency.

12. The system of claim 11, the computer system is further configured to:
    create a phase weighted mask for each axial section in the spectral analysis;
    calculate an optimal phase-shift angle for each phase weighted mask to minimize a difference between overlapping sections of phase-weighted masks in the phase optimization; and
    combine all the phase-weighted masks to form the three dimensional mask.

13. The system of claim 12, the computer system is further configured to:
    multiply the three dimensional mask by the filtered three dimensional image volumes; and
    sum the resulting three dimensional image volumes to estimate the second motion signal.

14. The system of claim 10, the computer system is further configured to:
    normalize the final motion signal; and
    obtain an optimal gate to correct for temporal variations in an amplitude of the final motion signal, wherein the optimal gate is the smallest amplitude range covering a pre-determined fraction of acquisition time of the final motion signal.

15. The system of claim 14, the computer system is further configured to:
- remove a frequency drift of the final motion signal by fitting a spline to the final motion signal;
- subtract the spline from the final motion signal;
- normalize the amplitude of the final motion signal; and
- perform baseline correction on the final motion signal.

16. An article of manufacture for deriving a respiratory signal from imaging data for continuous bed motion acquisition, the article of manufacture comprising a non-transitory, tangible computer-readable medium holding computer-executable instructions for performing a method comprising:
- acquiring a time-series of three dimensional image volumes;
- estimating a first respiratory signal through a measurement of distribution of each three dimensional image volumes;
- applying a spatial filter to the time-series of three dimensional image volumes, thereby yielding a plurality of filtered three dimensional image volumes;
- dividing the filtered three dimensional image volumes into a plurality of axial sections overlapping each other by a predetermined amount, wherein each axial section has a predetermined length;
- performing a spectral analysis on each axial section to locate a plurality of three dimensional image volumes which are subject to a respiratory motion;
- performing a phase optimization on each axial section to obtain a three dimensional mask;
- estimating a second respiratory signal through the three dimensional mask and the time-series of three dimensional image volumes, wherein the second respiratory signal has a consistent relationship between a polarity of a respiratory signal gradient and a direction of the respiratory motion; and
- estimating a final respiratory signal based on the first respiratory signal and the second respiratory signal.

17. The article of manufacture of claim 16, the method further comprising:
- multiplying the three dimensional mask by the filtered three dimensional image volumes; and
- summing the resulting three dimensional image volumes to estimate the second respiratory signal.

18. The article of manufacture of claim 16, the method further comprising:
- normalizing the final respiratory signal; and
- obtaining an optimal gate to correct for temporal variations in an amplitude of the final respiratory signal, wherein the optimal gate is the smallest amplitude range covering a pre-determined fraction of acquisition time of the final respiratory signal.

19. The article of manufacture of claim 18, the method further comprising:
- removing a frequency drift of the final respiratory signal by fitting a spline to the final respiratory signal;
- subtracting the spline from the final respiratory signal;
- normalizing the amplitude of the final respiratory signal; and
- performing baseline correction on the final respiratory signal.

20. The article of manufacture of claim 16, wherein at least two axial sections have different lengths, and at least two pairs of adjacent axial sections overlap by different amounts.

* * * * *